(12) United States Patent
Lipowsky et al.

(10) Patent No.: US 8,491,758 B2
(45) Date of Patent: Jul. 23, 2013

(54) PROCESS FOR INHIBITING POLYMERIZATION OF (METH)ACRYLIC ACID AND/OR (METH)ACRYLIC ESTERS

(75) Inventors: Gunter Lipowsky, Ladenburg (DE); Steffen Rissel, Kirchheim (DE); Volker Schliephake, Schifferstadt (DE); Ulrich Jäger, Römerberg (DE); Sylke Haremza, Neckargemünd (DE)

(73) Assignee: BASF SE, Ludwigshafen (DE)

( * ) Notice: Subject to any disclaimer, the term of this patent is extended or adjusted under 35 U.S.C. 154(b) by 282 days.

(21) Appl. No.: 12/963,920

(22) Filed: Dec. 9, 2010

(65) Prior Publication Data

US 2011/0140050 A1 Jun. 16, 2011

Related U.S. Application Data

(60) Provisional application No. 61/286,032, filed on Dec. 14, 2009.

(30) Foreign Application Priority Data

Dec. 14, 2009 (DE) .......................... 10 2009 058 058

(51) Int. Cl.
*C07C 69/54* (2006.01)
*C07C 7/05* (2006.01)
*C07C 7/20* (2006.01)
*C07C 53/15* (2006.01)
*B01D 3/42* (2006.01)
*B01D 3/00* (2006.01)

(52) U.S. Cl.
USPC .................. 203/9; 203/6; 203/8; 252/182.19; 252/183.12; 560/205; 560/244; 562/545; 562/600; 562/532

(58) Field of Classification Search
USPC .................. 203/6, 9, 8, DIG. 21; 252/182.29; 252/183.12; 560/205, 244; 562/545, 532, 562/600
See application file for complete search history.

(56) References Cited

U.S. PATENT DOCUMENTS

| | | | |
|---|---|---|---|
| 3,674,651 A | 7/1972 | Otsuki et al. | |
| 7,119,224 B2 * | 10/2006 | Schroeder et al. | 560/205 |
| 2004/0031674 A1 * | 2/2004 | Schroder | 203/2 |
| 2004/0050679 A1 * | 3/2004 | Hammon et al. | 203/6 |
| 2004/0138501 A1 * | 7/2004 | Thiel et al. | 562/600 |
| 2004/0225151 A1 * | 11/2004 | Yada et al. | 562/600 |
| 2005/0006219 A1 * | 1/2005 | Eck et al. | 203/1 |
| 2005/0261523 A1 * | 11/2005 | Schroder et al. | 562/602 |
| 2006/0142613 A1 * | 6/2006 | Yada et al. | 562/600 |
| 2011/0140050 A1 * | 6/2011 | Lipowsky et al. | 252/407 |

FOREIGN PATENT DOCUMENTS

| | | |
|---|---|---|
| DE | 2 202 980 | 7/1973 |
| DE | 2 362 373 | 7/1974 |
| DE | 196 04 253 A1 | 8/1997 |
| DE | 196 04 267 A1 | 8/1997 |
| DE | 197 46 689 A1 | 4/1999 |
| DE | 101 44 490 A1 | 3/2003 |
| DE | 102 00 583 A1 | 7/2003 |
| DE | 102 38 145 A1 | 11/2003 |
| DE | 102 56 147 A1 | 12/2003 |
| DE | 103 39 633 A1 | 4/2004 |
| DE | 103 39 336 A1 | 3/2005 |
| DE | 10 2005 030 416 B4 | 6/2007 |
| EP | 0 733 617 A1 | 9/1996 |
| EP | 1 035 102 A1 | 9/2000 |
| EP | 1 081 125 A1 | 3/2001 |
| EP | 1 084 740 A1 | 3/2001 |
| EP | 1 688 407 A1 | 8/2006 |
| WO | WO 01/38285 A1 | 5/2001 |
| WO | WO 02/090299 A2 | 11/2002 |
| WO | WO 2005/007610 A1 | 1/2005 |
| WO | WO 2006/092410 A1 | 9/2006 |

\* cited by examiner

*Primary Examiner* — Joseph D Anthony
(74) *Attorney, Agent, or Firm* — Oblon, Spivak, McClelland, Maier & Neustadt, L.L.P.

(57) ABSTRACT

A process for inhibiting polymerization of (meth)acrylic acid and/or (meth)acrylic esters by introducing an oxygenous gas into the (meth)acrylic acid and/or the (meth)acrylic ester, in which the (meth)acrylic acid and/or the (meth)acrylic ester has a degree of purity of at least 95% and is in the liquid state.

11 Claims, No Drawings

PROCESS FOR INHIBITING POLYMERIZATION OF (METH)ACRYLIC ACID AND/OR (METH)ACRYLIC ESTERS

CROSS REFERENCE TO RELATED APPLICATIONS

This application claims priority to U.S. provisional application Ser. No. 61/286,032, filed Dec. 14, 2009, the text of which is incorporated herein by reference. This application also claims priority to German patent application number 10 2009 058 058.1, filed Dec. 14, 2009.

The present invention relates to a process for inhibiting polymerization of (meth)acrylic acid and/or (meth)acrylic ester.

(Meth)acrylic monomers, especially (meth)acrylic acid and (meth)acrylic ester, are important compounds for preparation of polymers which are used in a wide variety of fields of use (for example as superabsorbent polymers for diapers, dispersions for adhesives, coating materials, colors, as paints and in the textile and paper industry sector).

In the context of this document, "(meth)acrylic acid" shall be understood to mean both acrylic acid and methacrylic acid, and "(meth)acrylic ester" to mean both acrylic ester and methacrylic ester.

It is common knowledge that polymerizable compounds such as (meth)acrylic acid and (meth)acrylic ester can be made to polymerize easily by heating or the action of light or peroxides. However, particularly in the course of preparation and workup, undesired polymerization occurs time and again in different plant parts, which necessitates shutdown and cleaning of the plant. There is therefore a constant need for novel, simple and economic methods of reducing polymerization.

Inhibition of polymerization is of significance especially when the polymerizable compound is present in high purity, for example acrylic acid with a degree of purity of at least 95%, and is in the liquid state.

It is widespread prior art that the polymerization of (meth)acrylic acid and (meth)acrylic esters can be suppressed by the use of polymerization inhibitors, frequently in conjunction with oxygenous gases.

For instance, German published specification DE 19 746 689 A1 discloses a process for preparing (meth)acrylic acid, in which oxygen in the form of air is metered into the column or into the evaporator.

EP 1 035 102 A1 discloses a process for purifying (meth)acrylic acid and (meth)acrylic esters, wherein an oxygenous gas is metered into the lines between column bottom and heat exchanger.

WO 01/38285 A1 discloses a process for purifying (meth)acrylic monomers by distillation. This uses a combination of a polymerization inhibitor soluble in a liquid, for example hydroquinone monomethyl ether (MEHQ) or phenothiazine (PTZ), of oxygen and $NO_2$. The oxygen is introduced into the distillation still in the form of air, while $NO_2$ is added to the feed and/or to the points in the column inaccessible to the liquid.

A process for workup of (meth)acrylic acid and (meth)acrylic esters, in which an oxygenous gas is introduced, is likewise known from DE 102 38 145 A1. The oxygenous gas is partly metered into the upper part of the distillation column and partly into the bottom of the column.

A particular embodiment of the metered addition of oxygen into the distillation column in a process for preparing (meth)acrylic acid and (meth)acrylic esters is disclosed by DE 103 39 336 A1. This involves metering the oxygenous gas in through orifices in ring lines installed on the particular column trays with an exit rate of at least 50 mm/s.

DE 102 56 147 A1 describes a process for rectificative separation of liquids comprising (meth)acrylic monomers in a rectification column. This involves withdrawing a stream from the column and, after treatment with air, feeding at least one substream of this stream as a liquid phase back to the rectification column. The oxygen content of this recycled stream is at least twice as high as that of the stream withdrawn. The air used to treat the stream is supplied via a saturator. In the inventive example, saturation is described in an empty tube open to the atmosphere with injection of the acrylic acid from a delay vessel and complete recycling to the column. This achieved an $O_2$ saturation of 45 ppm in acrylic acid.

EP 1 084 740 A1 discloses an apparatus which is suitable for introducing oxygenous gases. The arrangement disclosed therein, which is secured on the inside of an apparatus with a certain downward gradient, reduces polymerization.

The introduction of oxygenous gases into the bottom of the column in the case of preparation of (meth)acrylic acid and (meth)acrylic esters is likewise known from German published specifications DE 2 362 373 and DE 2 202 980, and from U.S. Pat. No. 3,674,651. According to these, the oxygenous gas is used in combination with other polymerization inhibitors, which may also be metered in separately from the oxygenous gas, for example via the top of the column.

DE 10 2005 030 416 A1 discloses an arrangement for treatment of polymerizable substances, which comprises at least one sparging apparatus for introducing a gas into the polymerizable substance and a heating apparatus. This comprises an upright tube bundle heat exchanger wherein the liquid flows from the top downward and the air is conducted in countercurrent from the bottom upward.

In the prior art cited, the oxygenous gases are generally metered into the bottoms, for example into the bottoms circulation system, in distillation columns or in reactors.

These processes have the disadvantage that they do not prevent the polymerization of (meth)acrylic acid and (meth)acrylic ester effectively enough. They are especially disadvantageous when the (meth)acrylic acid and/or the (meth)acrylic ester already has a high degree of purity, for example of at least 95%, and is in the liquid state.

EP 1 688 407 A1 discloses a process for purifying (meth)acrylic acid, wherein air is introduced in a tank (so-called reflux tank) which is filled with (meth)acrylic acid distillation condensate. In this way, stabilization is carried out. The excess air is removed through the offgas line of the tank.

However, the prior art does not disclose a process which discloses the metered addition of an oxygenous gas into a (meth)acrylic acid and/or (meth)acrylic ester between production or workup and tank dispensing, wherein the (meth)acrylic acid and/or the (meth)acrylic ester has a high degree of purity, for example of at least 95%, and is in the liquid state.

It was therefore an object of the present invention to provide a process for inhibiting polymerization of (meth)acrylic acid and (meth)acrylic esters, with which the polymerization thereof can be reduced more effectively than with the existing processes. The process should more particularly be effective against inhibition of polymerization when the (meth)acrylic acid and/or the (meth)acrylic ester already has a high degree of purity, for example of at least 95%, and is in the liquid state.

The object was achieved by a process for inhibiting polymerization of (meth)acrylic acid and/or (meth)acrylic esters by introducing an oxygenous gas into the (meth)acrylic acid and/or the (meth)acrylic ester, in which the (meth)acrylic acid and/or the (meth)acrylic ester has a degree of purity of at least 95% and is in the liquid state.

It is essential to the invention that the process for inhibiting polymerization finds use when the (meth)acrylic acid and/or the (meth)acrylic ester already has a high degree of purity of at least 95%, and is in the liquid state. This is the case especially for the workup of (meth)acrylic acid and/or (meth)acrylic esters which are drawn off through a side or top draw of the column after a distillative or rectificative purification in a column, condensed if necessary and supplied either to further workup or to dispensing in, for example, a tank.

Liquid (meth)acrylic acid and/or liquid (meth)acrylic ester with such a high degree of purity are at particular risk of polymerization. Even though this (meth)acrylic acid and/or (meth)acrylic ester is admixed with polymerization inhibitors, for example hydroquinone monomethyl ether or phenothiazine, both during the preparation and for the storage, the inhibition of polymerization is insufficient.

It has now been found that, surprisingly, the oxygen saturation in the liquid (meth)acrylic acid and/or the liquid (meth)acrylic ester is too low to bring about sufficient inhibition of polymerization in combination with customary polymerization inhibitors. This is surprising in that the overall preparation process and the workup already work in the presence of oxygenous gases. Therefore, in accordance with the invention, an oxygenous gas is passed into the liquid (meth)acrylic acid or the liquid (meth)acrylic ester, such that sufficient oxygen for the inhibition of polymerization is dissolved in the liquid (meth)acrylic acid or the liquid (meth)acrylic ester.

The preparation and workup of (meth)acrylic acid and (meth)acrylic esters is known per se. For example, the preparation of acrylic acid is described in DE 103 39 633 A1, WO 02/090299 A2, WO 05/007610 A1 and WO 06/092410 A1, and the literature cited therein. The documents DE 101 44 490 A1, EP 0 733 617 A1, EP 1 081 125, DE 196 04 267 and DE 196 04 253 A1, and the literature cited therein, also disclose the preparation of (meth)acrylic esters among other subject matter.

The purity of the (meth)acrylic acid and/or of the (meth)acrylic esters is generally at least 95%, preferably at least 97%. The compounds mentioned are in liquid form in the side or top draw of the column and therefore have to be condensed with a suitable condenser if required.

Glacial acrylic acid which is supplied, for example, to tank dispensing may have, for example, the following composition:

| | |
|---|---|
| Acrylic acid | 99.7-99.9% by weight |
| Acetic acid | 50-1500 ppm by weight |
| Propionic acid | 10-500 ppm by weight |
| Diacrylic acid | 50-1000 ppm by weight |
| Water | 50-1000 ppm by weight |
| Aldehydes and other carbonyls | 1-50 ppm by weight |
| Inhibitors | 100-300 ppm by weight |
| Maleic acid/anhydride | 1-20 ppm by weight |

(Meth)acrylic esters in the context of the present invention may, for example, be methyl, ethyl, n-propyl, isopropyl, n-butyl, sec-butyl, isobutyl, tert-butyl, pentyl, hexyl, octyl, 2-ethylhexyl, 2-propylheptyl, dodecyl, 2-hydroxyethyl, 4-hydroxybutyl, 6-hydroxyhexyl, dihydrocyclopentadienyl, 2-dimethylaminoethyl or cyclohexyl (meth)acrylate, and also ethylene glycol di(meth)acrylate, 1,4-butanediol di(meth)acrylate or 1,6-hexanediol di(meth)acrylate, trimethylolpropane triacrylate or pentaerythrityl tetraacrylate.

It will be appreciated that this concept is also applicable to other polymerizable compounds, for example styrene, vinyl acetate, vinyl propionate, allylacetic acid, vinylacetic acid, N-vinylformamide or N-vinylpyrrolidone.

The oxygenous gas used may be pure oxygen, or else mixtures of oxygen and one or more gases which are inert under the reaction conditions in any desired mixtures. For example, it is possible to use air or a mixture of air and a gas which is inert under the reaction conditions. The inert gas used may be nitrogen, helium, argon, carbon monoxide, carbon dioxide, steam, lower hydrocarbons or mixtures thereof. The oxygen content of the oxygenous gas is between 0.1 and 100% by volume, preferably between 1 and 50% by volume and more preferably between 3 and 21% by volume. Preference is therefore given to air or a mixture of air with a gas which is inert under the reaction conditions.

As already written, it is essential to the invention that the (meth)acrylic acid or the (meth)acrylic ester is in the liquid state. The temperature of the (meth)acrylic acid or of the (meth)acrylic ester at atmospheric pressure is therefore generally between 0 and 100° C., preferably between 20 and 90° C. and more preferably between 25 and 85° C. This of course applies only to such an extent that the (meth)acrylic acid or the (meth)acrylic ester is also in the liquid state at the temperatures mentioned and at atmospheric pressure, which means that the melting point and the boiling point are outside the range specified.

The amount of oxygen fed into the liquid (meth)acrylic acid or the liquid (meth)acrylic ester is not restricted. Typically, the oxygen feeding, however, is adjusted such that the oxygen content in the liquid (meth)acrylic acid or the liquid (meth)acrylic ester is between 0.3 and 56 ppm, preferably between 1 and 45 ppm and more preferably between 5 and 30 ppm.

The oxygen saturation in the liquid (meth)acrylic acid or the liquid (meth)acrylic ester depends on the oxygen content of the oxygenous gas. In liquid acrylic acid, on introduction of air (at 20° C. under atmospheric pressure), 100% oxygen saturation is achieved when the acrylic acid has an oxygen content of 56 ppm; on introduction of so-called lean air with an oxygen content of approx. 8%, 100% oxygen saturation is achieved at an oxygen content of liquid acrylic acid of 25 ppm. Using pure oxygen, in contrast, up to 280 ppm of oxygen are dissolved in the liquid acrylic acid.

In principle, it is necessary that the supply of the oxygenous gas is controlled. To this end, a sensor to determine the oxygen content in the liquid (meth)acrylic acid or the liquid (meth)acrylic ester has to be installed, in order to be able to determine therefrom the amount of oxygen still required and to be able to introduce it. Subsequently, the oxygenous gas introduced is controlled by virtue of all oxygenous gas supplied dissolving in the liquid (meth)acrylic acid or the liquid (meth)acrylic ester and no gas bubbles forming. If desired, a second sensor can subsequently be used to once again determine the oxygen content of the liquid (meth)acrylic acid or of the liquid (meth)acrylic ester.

In addition, the supply of the oxygenous gas can be regulated. For example, in the case of air, the supply is between 0.1 and 10 m$^3$/h, preferably between 0.5 and 6 m$^3$/h and particularly between 0.5 and 2 m$^3$/h. The supply is of course adjusted to the oxygen content of the oxygenous gas.

As described above, the oxygenous gas is supplied at the points in the process at which the (meth)acrylic acid and/or the (meth)acrylic ester has a high purity of at least 95% and is in the liquid state. This is the case especially in the workup of (meth)acrylic acid and/or (meth)acrylic esters which are drawn off through a side or top draw of the column after a distillative or rectificative purification in a column, condensed if necessary and sent either to further workup or to dispensing in, for example, a tank. Preference is therefore given to the introduction of an oxygenous gas into a line comprising liquid (meth)acrylic acid and/or liquid (meth)acrylic ester which is supplied as a pure product, after distillative or rectificative purification in a column, through a top or side draw to tank dispensing.

The process according to the invention is suitable with particular preference for acrylic acid as the pure product. The latter is typically passed as glacial acid in a line with a gradient to the tank for dispensing.

The metered addition of the oxygenous gas can be metered in at any possible point in the line. In order, however, to ensure sufficient inhibition of polymerization over the entire length of the line, the metered addition is effected in flow direction of the liquid (meth)acrylic acid or of the liquid (meth)acrylic ester, preferably in the front half, more preferably in the front third, of the line through which the pure product is conducted.

The oxygenous gas can be fed in via any desired devices which are suitable for the process according to the invention and are known to those skilled in the art.

For example, these devices may be curved or straight inserted or immersed tubes which may optionally be provided with further orifices, or nozzles or valves, or those devices as described in EP-A1 1 035 102. Preference is given, however, to inserted or immersed tubes optionally provided with further orifices. The devices are preferably mounted such that the orifices are immersed at least partly, preferably completely, into the liquid (meth)acrylic acid or the liquid (meth)acrylic ester, in order to dissolve a maximum amount of oxygen in the pure product.

The material from which the metering devices are manufactured is not crucial in accordance with the invention; it should be corrosion-stable to the pure product under the conditions which exist. They are preferably manufactured from stainless steel or copper or from copper-plated material; also conceivable are plastics which are stable under the conditions which exist, for example Teflon® or Kevlar®.

The orifices in the devices may, for example, be holes, slots, valves or nozzles, preferably holes of any shape, preferably round holes. The orifices may be distributed anywhere over the metering devices, for example on the underside and/or on the walls and/or randomly on the surface of the metering devices, preferably on the lower half thereof, more preferably on the underside. It will be appreciated that the devices may have a plurality of orifices, for example on the underside and distributed randomly over the surface of the metering devices.

Typically, the pure product is stabilized against polymerization with at least one stabilizer. This at least one stabilizer may already be present in the pure product after the distillative or rectificative workup, or is, when the stabilizer has been partly or completely removed by the purification, added again to the pure product.

Suitable stabilizers are, for example, phenolic compounds, amines, nitro compounds, phosphorus or sulfur compounds, hydroxylamines, N-oxyls and particular inorganic salts, and if appropriate mixtures thereof.

Very particular preference is given to phenothiazine, hydroquinone monomethyl ether and a mixture of hydroquinone monomethyl ether and phenothiazine.

If the addition of stabilizer is still required, the method of addition of the stabilizer is not restricted. The stabilizer added may in each case be added individually or as a mixture, in liquid form or dissolved in a suitable solvent, in which case the solvent itself may be a stabilizer, as described, for example, in German patent application DE 102 00 583 A1.

When a mixture of a plurality of stabilizers is used, they can each independently be supplied at the same or different metering sites among those mentioned above. When a mixture of a plurality of stabilizers is used, they may also each independently be dissolved in different solvents.

For sufficient inhibition of polymerization, it is necessary that the concentration of the stabilizer per individual substance may be between 1 and 10 000 ppm, preferably between 10 and 5000 ppm, more preferably between 30 and 1000 ppm, even more preferably between 50 and 500 ppm and especially between 100 and 300 ppm.

ppm and percentage figures used in this document relate, unless stated otherwise, to percentages and ppm by weight.

U.S. Provisional Patent Application No. 61/286,032, filed Dec. 14, 2009, is incorporated into the present patent application by literature reference. With regard to the abovementioned teachings, numerous changes and deviations from the present invention are possible. It can therefore be assumed that the invention, within the scope of the appended claims, can be performed differently than the way described specifically herein.

EXAMPLES

The oxygen measurement was carried out in all examples with the commercial Hamilton Oxygold measuring instrument equipped with a Knick-$O_2$-meter.

Example 1

In an industrial scale plant for preparing acrylic acid, consisting of a rectification column with separating internals (as described in Example 1 of DE 103 39 633 A1, diameter 3.8 m, length 32 m), a liquid acrylic acid with a purity of 99.6% and a temperature of 84° C. was drawn off in a side draw. The oxygen measurement was carried out after approx. 50 m of the side draw line with a substream of liquid acrylic acid in a pumped circulation system, and the acrylic acid had cooled to a temperature of 35° C. in the meantime. The oxygen measurement was carried out as described above. No oxygen was detected in the liquid acrylic acid.

Example 2

In the plant described in Example 1, air with a feed rate of in each case 1.5 m$^3$/h was metered into the substream of liquid acrylic acid (T=35° C.) from two lines in the pumped circulation system. The oxygen-enriched substream of acrylic acid was recycled to the start of the side draw line and mixed with the liquid acrylic acid which had been drawn off directly from the rectification column (T=75° C.). Subsequently, the oxygen measurement was carried out as in Example 1 after approx. 50 m of the side draw line. The oxygen content in the liquid acrylic acid was 0.3-0.4 ppm.

Example 3

In the plant described in Example 1, air was metered into the liquid acrylic acid (T=75° C.) at a feed rate of 1 m$^3$/h in the side draw line. The oxygen measurement was carried out as in Example 1 after approx. 50 m of the side draw line. The oxygen content in the liquid acrylic acid was 12 ppm.

Comparative Example

In the plant described in Example 1, the oxygen was metered onto the separating tray at the level of the side draw line. The oxygen measurement was carried out as in Example 1 after approx. 50 m of the side draw line. No oxygen was detected in the liquid acrylic acid.

The invention claimed is:

1. A process for inhibiting polymerization of a liquid state monomer, the process comprising:
    introducing an oxygenous gas into a line comprising the liquid state monomer,
    wherein the liquid state monomer
    is a liquid (meth)acrylic acid, a liquid (meth)acrylic ester, or a mixture thereof,
    is supplied, as a pure product, after a distillative or rectificative purification in a column through a top or side draw to tank dispensing, and
    has a degree of purity of at least 95%.

2. The process according to claim 1, wherein an oxygen content of the oxygenous gas is between 0.1 and 100% by volume.

3. The process according to claim 1, wherein an oxygen content of the oxygenous gas is between 1 and 50% by volume.

4. The process according to claim 1, wherein the oxygenous gas is air or a mixture of air with a gas which is inert under conditions of the polymerization.

5. The process according to claim 1, wherein an oxygen content of a total content of the oxygenous gas and the liquid state monomer is between 0.3 and 56 ppm.

6. The process according to claim 4, wherein a supply of air is between 0.1 and 10 $m^3/h$.

7. The process according to claim 6, wherein the supply of air is between 0.5 and 6 $m^3/h$.

8. The process according to claim 1, wherein the oxygenous gas is metered in a flow direction of the liquid state monomer at a front third of the line comprising the liquid state monomer.

9. The process according to claim 2, wherein the oxygen content of the oxygenous gas is between 1 and 50% by volume.

10. The process according to claim 1, wherein a supply of the oxygeneous gas is between 0.1 and 10 $m^3/h$.

11. The process according to claim 10, wherein the supply of the oxygeneous gas is between 0.5 and 6 $m^3/h$.

* * * * *